United States Patent [19]
Hennink et al.

[11] Patent Number: 5,985,573
[45] Date of Patent: Nov. 16, 1999

[54] CATIONIC POLYACRYLATES AND POLY (ALKYL) ACRYLATES OR THE CORRESPONDING ACRYLAMIDES FOR USE IN SYNTHETIC TRANSFECTION OR BLOCKING SYSTEMS

[75] Inventors: Wilhelmus Everhardus Hennink; Petra van de Wetering, both of Waddinxveen, Netherlands

[73] Assignee: Octoplus, B.V., Netherlands

[21] Appl. No.: 09/067,276

[22] Filed: Apr. 27, 1998

Related U.S. Application Data

[60] Provisional application No. 60/005,923, Oct. 27, 1995.

[30] Foreign Application Priority Data

Oct. 25, 1995 [EP] European Pat. Off. .............. 95202891
Oct. 25, 1996 [WO] WIPO ..................... PCT/NL96/00416

[51] Int. Cl.$^6$ .............................. C12Q 1/68; C12N 15/63; C07H 21/04
[52] U.S. Cl. ........................... 435/6; 435/320.1; 435/455; 435/458; 536/23.1
[58] Field of Search ........................... 435/6, 320.1, 455, 435/458; 536/23.1

[56] References Cited

FOREIGN PATENT DOCUMENTS

0 424 688  9/1990  European Pat. Off. .
0 463 508  6/1991  European Pat. Off. .
0 544 292  11/1992 European Pat. Off. .

*Primary Examiner*—Nancy Degen
*Assistant Examiner*—William Sandals
*Attorney, Agent, or Firm*—Morrison & Foerster, LLP

[57] ABSTRACT

The present invention relates to a synthetic transfection or blocking system comprising as a carrier a cationic, water soluble or water dispersable polyacrylate, a polyacrylamide, a poly($C_{1-6}$ alkyl)acrylate or poly($C_{1-6}$ alkyl)acrylamide. In addition, it relates to a method for introducing DNA fragments in target cells, comprising contacting these DNA fragments with a polyacrylate, a polyacrylamide, a poly($C_{1-6}$ alkyl)acrylate or poly($C_{1-6}$ alkyl)acrylamide, which is at least partially substituted with cationic substituents and subsequently contacting the obtained transfection system with target cells. Finally, the invention involves the use of a polyacrylate, a polyacrylamide, a poly($C_{1-6}$ alkyl)acrylate or poly($C_{1-6}$ alkyl)acrylamide, which is at least partially substituted with cationic substituents as a DNA carrier system.

12 Claims, 10 Drawing Sheets

MMA

NVP

PEGMA  n=4.5 trEGMA  n=3

CATIONIC POLYACRYLATES AND POLY (ALKYL) ACRYLATES OR THE CORRESPONDING ACRYLAMIDES FOR USE IN SYNTHETIC TRANSFECTION OR BLOCKING SYSTEMS

This application was filed under 35 USC §111 claiming priority under 35 USC §120 from PCT application PCT/NL96/00416 filed Oct. 25, 1996 which designates the U.S. and which claims priority from European Application 95/202891.5 filed Oct. 25, 1995 and from U.S. Provisional Application 60/005,923 filed Oct. 27, 1995.

The present invention relates to the field of synthetic transfection or blocking systems useful in the delivery of gene constructs or DNA fragments to cells, especially to cells in living organisms. More in particular the invention relates to cationic polymers having broad possibilities to be modified or adapted in order to create a flexible DNA or gene delivery system, which can be used in e.g., gene therapy applications.

Gene therapy is seen as a promising method to correct hereditary defects or to treat life threatening diseases such as cancer and AIDS. In gene therapy, nucleic acid fragments or gene constructs are brought into target cells in order to compensate for a missing gene or to introduce a new functionality in such cells. These nucleic acid fragments or gene constructs are preferably incorporated in plasmids.

If reconstructed plasmids are applied to an organism per se. this generally leads to low expression of the introduced gene, if any. There are three main reasons for this low expression. First, the plasmids will hardly ever reach the cell population where they are intended to be incorporated, due to degradation and elimination processes.

Second, if the plasmids do reach the target cells, they cannot simply pass the cellular membrane, because of the strongly polar nature and the size of the plasmids. Third, if a plasmid does invade a target cell, it normally will be enclosed in an endosome, which will convert into a lysosome. In the lysosome, the plasmid will be degraded so that the incorporated gene cannot be expressed.

For the above reasons, in gene therapy plasmids or other gene constructs are complexed with a carrier or vehicle.

In recent years, many efforts have been made in the research on potentially suitable transfection systems, both of viral and non-viral (cationic lipids and cationic polymers) origin. These transfection systems should deliver the desired gene or DNA fragment to the target cell and cause it to be expressed to a high degree.

Viral vectors are very suitable, because by nature adapted, to introduce plasmids in target cells and to avoid the degradation of the plasmids or the transition of endosomes into lysosomes. However, viral vectors have a number of pronounced disadvantages. Viral vectors are able to effect integration of the introduced gene in the chromosomal DNA of the target cell. The site where this integration is effected cannot (yet) be predicted or controlled, which may, for instance, involve the risks of destroying essential genes and of activating oncogenes. In addition, it is at present very difficult to provide for viral vectors on a commercial scale. Moreover, viral vectors generally trigger the immune system of a living organism, which will lead to immuno responses against the transfection system when used in vivo. Finally, viral vectors inherently set limits to the size of the gene construct to be introduced in the target cell.

In order to overcome the intrinsic disadvantages of viral vectors, synthetic transfection systems should offer good perspectives.

In this light, explicit reference is made to research carried out by the group of E. Wagner, relating to gene delivery by means of plasmid-polylysine complexes (Curiel et al. Adenovirus Enhancement of Transferrin-Polylysine-Mediated Gene Delivery, Proc. Natl. Acad. Sci. 88 (1991) 8850–8854; Plank et al. Gene Transfer into Hepatocytes Using Asialoglycoprotein Receptor Mediated Endocytosis of DNA Complexed with an Artificial Tetra-Antennary Galactose Ligand Bioconj. Chem. 3 (1992) 533–539; Wagner et al. Influenza Virus Hemagglutin HA2 N-Terminal Fusogenic Peptides Augment Gene Transfer by Transferrin-Polylysine-DNA Compleses: Toward a Synthetic Virus-like Gene-Transfer Vehicle, Proc. Natl. Acad. SC4. 89 (1992) 7934–7938; and Curiel et al. Gene Transfer to Respiratory Epithelial Cells via the Receptor Mediated Endocytosis Pathway, Am. J. Respir. Cell Mol. Biol. 6 (1992) 247–252). The plasmid-polylysine complex investigated upon exposition to certain cell lines showed at least some expression of the gene. Further, it was found that the expression efficiency increased considerably due to the binding of transferrin to the plasmid-polylysine complex. Transferrin gives rise to close cell-complex contact with cells comprising transferrin receptors; it binds the entire complex to the transferrin receptor of cells. Subsequently, at least part of the entire complex was found to be incorporated in the cells investigated.

However, the transfection efficiency of these polylysine based transfection systems as well as other known synthetic transfection systems is much lower than the efficiency of the known viral vectors.

The aim of the present invention is to provide for an effective and efficient synthetic transfection or blocking system. In order to be able to bind and condense DNA, e.g. in the form of a plasmid, wherein a gene construct is incorporated, the carrier system should possess a positive charge at physiological pH.

It has now been found that such a system can be based on polyacrylates, polyacrylamides, poly($C_{1-6}$ alkyl)acrylates or poly($C_{1-6}$ alkyl)acrylamides which contain cationic substituents. More in particular, the invention relates to water soluble or water dispersible polyacrylate, polyacrylamide, poly(lower alkyl)acrylate or poly(lower alkyl)acrylamide based transfection systems, wherein organic cationic moieties are attached to the polyacrylate or poly(alkyl)acrylate backbone or the backbone of the corresponding acrylamides. With the term "lower alkyl" it is intended to refer to $C_{1-6}$ alkyls, preferably $C_{1-4}$ alkyls.

The polymer which forms the basis of the carrier system of the present invention essentially comprises a backbone of —[—$CH_2$—$C(R_1)(COOR_2)$—]$_n$— units, wherein all $R_1$-groups may be the same or different and represent hydrogen atoms or straight or branched $C_{1-6}$ alkyl groups, and wherein all $R_2$-groups may be the same or different and are selected so that the net charge of the polymer corresponds to the charge of at least 5 mole % cationic groups.

With the phrase "so that the net charge of the polymer corresponds to the charge of at least 5 mole % cationic groups" it is meant that under physiological conditions at least 5 mole % of the units bear a cationic group if the other units are neutral or at least (5+x) mole % bear a cationic group if x mole % of the other units bear an anionic group. If $R_2$ does not represent a group which is cationic under physiological conditions, it may be selected from a large number of different groups, such as hydrogen atoms, aryl groups, glycol groups, $C_{1-6}$ branched or linear alkyl groups, which may be substituted by inert substituents, such as halogen atoms, etc.

Preferably, the cationic groups $R_2$ are of the formula $—R_3—N(R_4)(R_5)$, wherein $R_3$ represents a $C_{1-6}$ alkylene group or a $C_6H_4$ aromatic group, in which groups the hydrogen atoms may be replaced with inert substituents, and wherein $R_4$ and $R_5$, which may be the same or different, represent a hydrogen atom, a $C_{1-6}$ alkyl group or an aryl group.

A restricted number of other units than the $—[—CH_2—C(RI)(COOR_2)—]_n—$ units, such as pyrrolidone units may, however, be present in the backbone polymer.

Instead of the afore-mentioned acrylate moieties, acrylamide moieties can be present, preferably moieties of the formula $C(O)NR_4R_5$.

In order to be able to bind to and condense plasmids, gene constructs, oligonucleotides or other DNA fragments, the polyacrylates, polyacrylamides, poly(alkyl)acrylates or poly ($C_{1-6}$ alkyl)acrylamides used must—at physiological pH—at least contain 5 mole % cationic groups $R_2$ (net charge) coupled to the backbone. In these cases, the poly acrylate amide or poly (alkyl)acrylate amide is able to bind DNA electrostatically and condense therewith. In addition, it appeared that such cationic polymer-DNA complexes are taken up in the target cells in a considerably higher amount as compared with the plasmids per se.

As said herein above, the cationic group is preferably formed by a moiety of the formula $—R_3—N(R_4)(R_5)$, most preferably by dimethyl amino ethyl groups or $—(R_4)(R_5)$ if coupled to the acrylamide group.

Other suitable cationic substituents $R_2$ are preferably derived from organic moieties possessing an amino group. Such moieties are positively charged at physiological pH. Examples of these organic moieties are amino $C_{1-10}$ alcohols, and amino $C_{1-10}$ alkoxy $C_{1-10}$ alcohols, as well as their secondary, tertiary and quaternary derivatives. Especially, tertiary amines are preferred.

Dimethylamino ethyl groups, as well as other tertiary amines, will at least partially be protonated under physiological conditions, yielding a cationic structure which is able to bind and condense DNA.

Although it is important that the polymer is positively charged as a whole, it is preferred that the substituents $R_2$ of the acrylic/(alkyl)acrylic acid or amide units in the backbone do not entirely comprise cationic moieties. In a preferred embodiment, part of the backbone units, preferably at least 10 mole %, comprises other hydrophobic and hydrophilic moieties. The transfection or blocking system of the present invention therefore is based on both homopolymers of acrylates, acrylamides, ($C_{1-6}$ alkyl)acrylates or (alkyl) acrylamides, copolymers comprising different acrylate, acrylamide, (alkyl)acrylate or (alkyl)acrylamide units, and copolymers of acrylate, acrylamide, (alkyl)acrylate or (alkyl)acrylamide and other units such as methylmethacrylate, triethylene glycol methacrylate, and poly ethylene glycol methacrylate, hydroxyethylmethacrylate, glycerylmethacrylate, laurylmethacrylate, butylmethacrylate, N-isopropylacrylamide, N-(3-dimethylamino)propyl) methacrylamide and so on. As said herein above, it is not necessary that all backbone units represent acrylate-like moieties. A part of the units may be formed by e.g. N-vinyl pyrrolidone or vinyl acetate.

Copolymers which contain N-isopropylamide units possess LCST (lower critical solution temperature) behaviour. This means that the polymer dissolves well in water at relatively low temperature, whereas at a temperature higher than the LCST phase separation occurs. In this light, reference is made to H. Feil et al. Macromolecules 26 (1993), 2496–2500. The inventors have indications that this LCST behaviour favorably affects the condensation process of polymer/plasmide particles.

In fact, especially good results are obtained when at least 10 mole % of the substituents $R_2$ are derived from essentially electrically neutral organic hydrophilic substituents such as glycerol, methoxy ethoxy ethanol and polyethylene glycol. A possible explanation for these advantageous results is that the plasmid will be less tightly bonded to the polymer, so that it can dissociate easier in the target cell. Further, it is noted that PEG avoids recognition by macrophages.

The polymer used in accordance with the present invention is of a cationic nature, and it is water soluble or water dispersible. More in particular, very good results are obtained if 5–100 mole % of the substituents $R_2$ represent a cationic moiety and 95–0 mole % of the substituents $R_2$ represent an anionic or neutral moiety, bearing in mind that the net overall charge should be cationic.

The molecular weight and/or number of the polymers used can be easily adjusted to the nature of the plasmid to be transported. Normally, polymers having a molecular weight of from 1,000 to 500,000 can suitably be used as a DNA carrier.

The weight ratio of the carrier polymers to the DNA fragments seems critical. Suitable results are obtained when using weight ratios of between 0.1 and 200; preferably a weight ratio of between 1 and 20, most preferably between 2 and 5 is used. The molecular weight of the acrylate or (alkyl)acrylate polymers can be controlled by using and maintaining suitable reaction conditions in the polymerization process. Preferably, the molecular weight of the cationic polymers used in accordance with the present invention is higher than 80.000 Da, preferably higher than 100.000 Da, most preferably higher than 250.000 Da.

The synthetic transfection system of the invention which comprises at least one cationic, water soluble or water dispersible polyacrylate, polyacrylamide, poly($C_{1-6}$ alkyl) acrylate or poly($C_{1-6}$ alkyl)acrylamide as a carrier further comprises a DNA fragment such as a plasmid, a gene construct or an oligonucleotide. Oligonucleotides can be uses as blocking structures, e.g., for controlling protein synthesis, in cells.

It is noted that the condensed particles comprising the poly acrylate based polymer and DNA fragments can be enclosed or incorporated in known drug delivery systems, e.g. in liposomes or hydrogels.

Genes to be incorporated into carrier systems or vehicles to be used in the synthetic transfection system are among others documented in McKusick, V. A. Mendelian inheritance in man, catalogs of autosomal dominant, autosomal recessive, and X-linked pheno-types. Eighth edition. John Hopkins University Press (1988).

Stanbury, J. B., Wyngaarden, J. B., Frederickson, D. S., Goldstein, J. L. and Brown, M. S. The metabolic basis of inherited disease. Fifth edition. McGraw-Hill (1983).

Vehicles to be used in embodiments of the present invention include viral and non-viral regulatory elements for expression and/or replication. These vehicles are well known in the field.

Suitable transfection systems are able to target a gene construct to the aimed cell population. The polyacrylate, polyacrylamide, poly(alkyl)acrylate or poly(alkyl) acrylamide based transfection system of the invention therefore preferably comprises at least one group that selectively recognizes proteins associated with the surface of the target cells. Such targeting moieties or homing devices are known to the skilled person and comprise, e.g., tri and tetra antennary cluster glycosides, transferrin or other protein constructs, monoclonal antibodies against cell membrane proteins, ligands for cell surface associated receptors and binding fragments of derivatives of said targeting moieties, etc. If, for instance, galactose moieties are coupled to the polyacrylate or poly(alkyl)acrylate system of the present invention the transported gene fragments are delivered to hepatocytes through the galactose receptor of hepatocytes. Furthermore, the presence of recognizable structures covalently or non-covalently coupled to the polymer part of a polymer-DNA complex facilitates the incorporation of the DNA fragment, e.g., a gene construct, in the target cell.

Moreover, the transfection system can be adapted to allow the gene construct to leave endosomes in the cellular system. Thereto membrane destabilizing structures, in particular polypeptide fragments, are conjugated to the water soluble or water dispersible cationic polymer systems of the invention. Such destabilizing structures should be able to disturb or destabilize the endosomal membrane systems. The plasmids incorporating a gene construct so reach the cytoplasm of the target cell, where the gene construct can be expressed in the nucleus. Examples of such membrane destabilizing structures which are suitably used in accordance with the present invention are fusogenic structures, e.g. certain peptides and (parts of) viral coating proteins, for instance peptides derived from hemagglutinin protein of the influenza virus (see in this respect, e.g., Plank et al. The Influence of Endosome-Disruptive Peptides on Gene Transfer Using Synthetic Virus-Like Gene Transfer Systems, J. Biol. Chem. 269 (1994), 12918–12924).

Other compounds useful in accordance with the present invention are endosome destabilizing compounds such as chloroquine. It is noted that chloroquine is only used in in vitro applications, because it is toxic in vivo. Since the invention is directed to both in vivo and in vitro applications, this embodiment is within the scope of the invention.

The poly acrylates, polyacrylamides, poly($C_{1-6}$ alkyl) acrylates or -acrylamides which are used as a DNA carrier in accordance with the present invention are known per se. This also applies to methods of preparing these polymers. A preferred method to prepare these polymers is radical polymerisation of acrylic or ($C_{1-6}$ alkyl)acrylic acid derivatives, e.g. by using 2,2'-azoisobutyronitrile (AIBN) as initiator, in a suitable solvent such as toluene, acetonitrile, DMSO, or THF. In addition, water can be used as a solvent, however, in that case, one cannot use AIBN. Suitable preparation techniques are described in G. Odian, Principles of Polymerization, Chapter 3 "Radical Chain Polymerization", John Wiley and Sons, Inc. New York (1991) as well as in references to which This handbook refers.

Preferably, the radical polymerization is carried out in the presence of a chain transfer reagent, e.g. β-mercapto ethanol, 2-aminoethane thiol or mercapto acetic acid. Copolymers can be obtained by mixing monomers in the desired ratios and amounts and subsequently subjecting this mixture to radical polymerization.

The method described has the additional advantage that it provides polymers or copolymers containing terminal functional groups, such as OH—, —$NH_2$ or COOH groups. These functional groups can suitably be used in a subsequent coupling step, wherein a homing device, such as a monoclonal antibody, or a fusogenic structure is introduced.

Fusogenic peptides and targeting molecules can be bound to the poly(alkyl) acrylates using well-known techniques, for instance using thiol groups introduced in the polymer and maleimide groups introduced in the peptide or targeting molecule. The homing device and/or fugogenic peptides can also be coupled to the polymer-plasmid complex via the well-known avidin-biotin coupling technique.

The delivery systems themselves can easily be prepared by contacting the polymers and the DNA fragments under conditions where the polymer is positively charged, preferably at a pH of 7.2 in a suitable buffer system (e.g. a PBS or HEPES buffer) at room temperature.

In a preferred embodiment the polymer-polynucleotide complexes are prepared in the presence of a viscosity increasing substance, preferably in the presence of sucrose. The addition of a viscosity increasing substance makes it possible to obtain smaller particles as is illustrated in Example 6.

The preparation of the delivery system normally is completed within 10 minutes complexation time. The preparation step can be followed by a separation step wherein the DNA polymer complex is separated from the unbound polymer. In a subsequent step the complex comprising DNA and the carrier polymer of the invention can be lyophilisized, preferably in the presence of a pharmaceutically acceptable cryoprotectant such as sucrose or mannitol. In lyophilisized condition the complex can be stored for a long period of time.

The present invention relates also to a method for the preparation of a synthetic transfection or blocking system comprising contacting polynucleotide fragments with a cationic water soluble or water dispersible polyacrylate or poly($C_{1-6}$ alkyl)acrylate, or the corresponding acrylamides as defined in any one of claims 1-7 under conditions wherein the polymer is positively charged. Preferably, the contacting is carried out in the presence of a viscosity increasing substance, preferably sucrose. Further the invention relates to the polynucleotide/polymer particles obtained in this way.

In a further embodiment, the invention relates to a method for introducing DNA fragments in target cells, comprising contacting these DNA fragments with a polyacrylate, a polyacrylamide, a poly(alkyl)acrylate, or a poly(alkyl) acrylamide, which is at least partially substituted with cationic substituents and subsequently contacting the obtainer transfection system with target cells.

Finally, the invention relates to the use of a polyacrylate, a polyacrylamide, a poly($C_{1-6}$ alkyl)acrylate or a poly($C_{1-6}$ alkyl)acrylamide, which is at least partially substituted with cationic substituents as transfection vehicle.

The carrier system of the present invention can be used both in in vivo and in in vitro applications.

The present invention will be described in further detail while referring to the following examples.

EXAMPLE 1

The synthesis of poly(dimethyl aminoethyl methacrylate) (P(DMAEMA)) homo and copolymers P(DMAEMA) homo and copolymers were routinely synthesized by radical polymerisation of DMAEMA, and optionally comonomers, using 2,2'-azoisobutyronitrile (AIBN) as the initiator in toluene as the solvent.

In detail, DMAEMA (Fluka, cat. no. 64140) was purified by distillation under reduced pressure. 5 ml of the purified DMAEMA were mixed with 20 ml toluene and transferred to a bottle (volume 30 ml) which was subsequently closed with a silicone rubber septum and flushed with $N_2$. AIBN (Fluka cat no 11630) was added and the polymerizing solution was incubated while shaking at 60° C. for 22 hours.

Copolymers of DMAEMA were synthesized by replacing part of the DMAEMA by another monomer. The following comonomers were copolymerized with DMAEMA: methyl methacrylate (MMA: Fluka cat. no. 64200), N-vinyl-2-pyrrolidone (NVP: Acros, cat. no. 1409227), ethoxytriethylene glycol methacrylate (triEGMA; PolySciences, cat. no. 18556), and poly(ethylene glycol)monomethylether monomethacrylate (PEGMA, PolySciences, cat. no. 16664).

To tailor the molecular weight of the (co)polymers, different monomer/initiator ratios were applied, or more effectively a chain transfer reagent (g-mercaptoethanol, 2-aminoethane thiol or mercapto acetic acid) was used. The latter method has an additional advantage that it provides copolymers which contain a terminal functional group (OH, $NH_2$ or COOH) which can be used for the subsequent coupling of a homing device (e.g. a monoclonal antibody) or fusogenic structures (e.g. peptides).

The polymers were precipitated from the reaction mixture using a suitable non-solvent (e.g. petroleum ether or diethylether) and collected by filtration. After drying under reduced pressure, the polymers were dissolved in water acid acidified with acetic acid and extensively dialyzed against water to remove (traces of) organic solvents and monomer. The polymer was thereafter collected by lyophilization. If the polymerization reaction is effected in DMSO, one can simply pour out the mixture in water. The aqueous mixture is evaporated and lyophilized in known ways.

The polymers were characterized by GPC and NMR.

GPC (gel permeation chromatography) analysis was carried out to determine the molecular weights (relative to polystyrene (solvent THF) or dextran (solvent 0.7 M $NaNO_3$, 0.1 M Tris/HCl, pH 7.0 in water); number average, $M_n$ and weight average, $M_w$) and molecular weight distribution of the P(DMAEMA) homo and copolymers. NMR (nuclear magnetic resonance) analysis was used to establish the copolymer composition.

More in detail, the polymerization conditions and results are depicted in the following table.

TABLE 1

Polymerization conditions for PDAEMA and copolymers

| DMAEMA (mol) | comonomer (mol) | monomer/initiator mol comonomer | feed composition mol DMAEMA/ mol comonomer | copolymer composition* mol DMAEMA/ mol comonomer | molecular weight** Mw | Mn | remarks |
|---|---|---|---|---|---|---|---|
| | | | MMA | | | | |
| 0.023 | 0.0093 | 250 | 2.47 | 2.6 | 19000 | 2600 | solvent: 20 ml toluene |
| 0.017 | 0.019 | 250 | 0.89 | 0.96 | 36000 | 3200 | polymerization time: 22 hr |
| 0.012 | 0.028 | 250 | 0.43 | 0.43 | 52000 | 3600 | polymerization temp. 60° C. |
| 0.0058 | 0.037 | 250 | 0.16 | 0.17 | 73000 | 4000 | nitrogen atmosphere initiator: AIBN |
| | | | VP | | | | |
| 0.023 | 0.0088 | 280 | 2.6 | 10.4 | ND | ND | solvent: 20 ml toluene |
| 0.017 | 0.018 | 300 | 0.96 | 3.6 | ND | ND | polymerization time: 22 hr |
| 0.012 | 0.026 | 330 | 0.45 | 1.4 | ND | ND | polymerization temp. 60° C. |
| 0.0058 | 0.035 | 350 | 0.16 | 0.3 | ND | ND | nitrogen atmosphere initiator: AIBN |
| | | | triEGMA | | | | |
| 0.023 | 0.0041 | 1200 | 5.6 | 6.7 | 65000 | 38000 | solvent: 20 ml toluene |
| 0.017 | 0.0083 | 220 | 2.1 | 2.4 | 51000 | 28000 | polymerization time: 22 hr polymerization temp. 60° C. nitrogen atmosphere |
| | | | PEGMA | | | | |
| 0.023 | 0.0033 | 250 | 7.0 | 8.3 | 13000 | 7100 | solvent: 20 ml toluene |
| 0.017 | 0.0066 | 240 | 2.7 | 2.8 | 20000 | 8100 | polymerization time: 22 hr polymerization temp. 60° C. nitrogen atmosphere |

TABLE 1-continued

Polymerization conditions for PDAEMA and copolymers

| DMAEMA (mol) | CTA*** (mol) | monomer/CTA ratio (mol/mol) | molecular weight** Mw | Mn | remarks |
|---|---|---|---|---|---|
| 0.030 | 0.0033 |  | 120000 | 55000 | solvent: non |
| 0.030 | 0.0066 | 250 | 37000 | 17000 | polymerization time: 22 hr |
| 0.030 |  | 125 | 22000 | 11000 | polymerization temp. 60° C. |
| 0.030 |  | 62 | 12000 | 6700 | nitrogen atmosphere |

*determined by NMR
**relative to polystyrene as determined by Gel Permeation Chromotagraphy
***chain transfer reagent (beta mercaptoethanol)
MMA     methyl methacrylate
VP     vinyl pyrrolidone
triEGMA     ethoxyl triethyleneglycol methacrylate
PEGMA     poly(ethyleneglycol)n monomethyl ether monomethacrylate (remark: NMR analysis showed that n = 4.5)

EXAMPLE 2
Transfection experiment comparing polymers of the invention with DEAE dextran, poly-lysine and Lipofectin®

COS cells (derived from African monkey kidney cells, provided by J. C. Clevers, Department of Immunology, Academic Hospital Utrecht) were cultured in Dulbecco's Modified Essential Medium (DMEM, Gibco cat. no. 31885) containing 3.7 g/l sodium bicarbonate, 0.58 g/l L-glutamine and 1 g/l glucose and supplemented with 100 U/ml penicillin; 100 μg/ml streptomycin, 0.25 μg/ml amphotericin B (Gibco cat. no. 15240) and 5% (v/v) heat-inactivated Fetal Bovine Serum (FBS, Bockneck).

To ensure log phase growth the cells were diluted by passaging at approximately 50% of their maximum density two days before transfection. 24 hours before transfection, these cells were seeded at $3 \cdot 10^4$ cells per $cm^2$ in 96 well plates ($14 \cdot 10^4$ cells per well).

The plasmid p(CMV.LacZ) was obtained from A. Bout (IntroGene Rijswijk). This plasmid is described in Exp. Lung Res 19 (1993) 193–202. This plasmid contains the LacZ gene controlled by the cytomegalovirus promoter/enhancer. This gene encodes for β-galactosidase.

The plasmid was propagated in *E. coli*, purified using a Qiagen-kit 2500 (Qiagen, cat. no. 12181) and diluted to 2 mg/ml with 10 mM Tris/1 mM EDTA buffer (TE, pH 8). Subsequently, it was stored at −20° C. or 4° C.

Transfection systems were prepared by incubation of the carrier and plasmid in a buffer solution (pH 7.2) at room temperature for a varying time period. The following polymers prepared in Example 1 were used: P(DMAEMA), P(DMAEMA-co-NVP), P(DMAEMA-co-MMA), P(DMAEMA-co-triEGMA), P(DMAEMA-co-PEGMA). Reference is made in this respect to schemes 1 and 2 of the drawings. DEAE dextran (Pharmacia, cat. no. 17-0350-01) and poly-L-lysine (synthesized via a ring opening polymerization or NCA-lysine initiated with triethyl amine in dry dioxane essentially according to E. R. Blout, J. Am. Chem. Soc. 83, 709– 712, 1961; $M_W$=1.2 $10^5$ g/mol) were used as reference carriers. A commercial cationic lipid formulation (Lipofectin®, Gibco, cat no. 18292) was used as well.

In detail, the polymers were dissolved in PBS (phosphate buffered saline, 0.9% NaCl, 10 mM phosphate, pH 7.2) to a concentration 1–2.5 mg/ml and diluted with transfection medium (plain Hepes buffered RPMI 1640 (Gibco, cat. no. 22511) 2% v/v FBS and 100 μM chloroquine to a concentration of 100 μg/ml. The plasmid stock solution (2 mg/ml; see above) was diluted with transfection medium to a concentration of 20 μg/ml.

x μl of this solution was pipetted into an Eppendorf tube, y μl transfection medium was added, followed by z μl of polymer solution; final concentration of plasmid ranges from 0 to 0.5 μg/ml; polymer 0 to 200 μg/ml. The plasmid/carrier complexes were allowed to form in 15–60 minutes at room temperature.

Immediately before transfection, the culture medium was aspirated from the cells. The cells were washed with RPMI and covered with 285 μl plasmid/carrier complex.

After 1–1.5 hours of incubation at 37° C. (5% $CO_2$, humidified atmosphere) the transfection medium was replaced by 100 μl culture medium (37° C.). The experiments were carried out in duplo using two separate plates.

After an additional 48 hours of incubation one plate was used to establish the cell viability and proliferation (XTT assay, see below); the other plate was used to determine the number of transfected cells (β-galactosidase staining).

In order to determine the number of transfected cells, the cells were rinsed with 100 μl PBS buffer and subsequently fixed with 75 μl 0.25% glutaraldehyde (Fluka, cat no. 49630) solution in PBS at 4° C. After an incubation time of 5 minutes, the fixative was removed and the cells were washed twice with PBS and the incubated with 50 μl staining solution containing 1 mg/ml 5-bromo-4-chloro-3-indolyl-β-D-galactopyranoside (X-Gal, Gibco, cat. no. 15520) 5 mM potassium ferrocyanide (Merck, cat. no. 104984), 5 mM potassium ferricyanide (BDH, cat. no. 10204) and 2 mM magnesium chloride (Merck, cat no. 5833) in 0.2 M sodium phosphate buffer (pH 7.4). After incubation for 30–50 minutes at 37° C. the cells were washed with PBS (covered with which preservative) and examined microscopically.

Transfected nuclei were clearly visible as blue spots using a microscope. The number of transfected cells per well (0.38 $cm^2$) was determined by counting.

To determine the influence of plasmid/carrier complexed on cell viability and proliferation, the number of living cells was measured using a XTT colorimetric assay essentially according to Boehringer's protocol (Cell Proliferation Kit II (XTT) cat. no. 1465015).

To each well 50 μl XTT labeling mixture containing 0.3 mg/ml sodium 3'-[1-(phenylaminocarbonyl)-3,4-tetrazolium]-bis(4-methoxy-6-nitro) benzene sulfonic acid hydrate (XTT, Sigma, cat. no. X4251) and 2.6 μl/ml N-methyl dibenzopyrazine methyl sulfate (PMS, Sigma, cat. no. 9625) in plain RPMI were added (total volume 150 μl). The cells were incubated for 1–3 h (37° C., 5% $CO_2$ and humidified atmosphere) and the formed formazan dye was Quantified spectrophotometrically using an ELISA plate reader measuring the absorbance at 490 nm with reference wavelength 655 nm. A calibration curve was established with fresh (living) cells (0–15*$10^4$ cells per well) and used to calculate the number of viable cells after transfection.

EXAMPLE 2a

Figure 1:
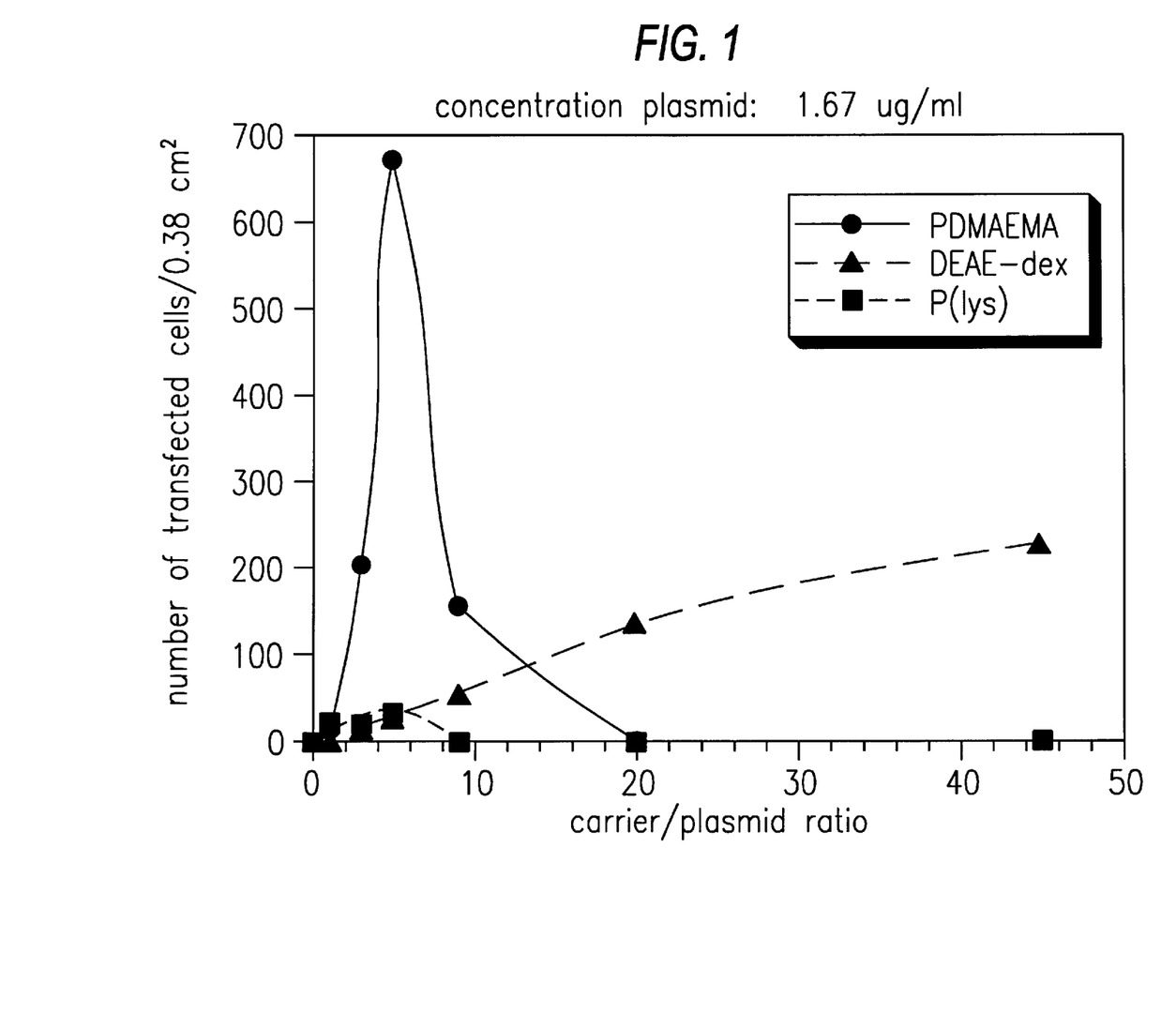
FIG. 1 shows the results of a gene transfer experiment in which P(DMAEMA) was compared with two known gene transfer polymers (DEAE-dextran and polylysine)

FIG. 1 shows the results of a gene transfer experiment in which P(DMAEMA) was compared with two known gene transfer polymers (DEAE dextran and poly-lysine). In this experiment the concentration of plasmid was fixed at 1.67 µl/ml; the concentration of polymer was varied. From this figure it can be concluded that P(DMAEMA) is a much better polymeric carrier for gene transfer than both p(lys) and DEAE-dextran. The number of transfected cells under optimal conditions (ratio PDAEMA/plasmid around 5) is about 700 which means that 1–2% of the total number of cells is actually transfected.

Figure 2:
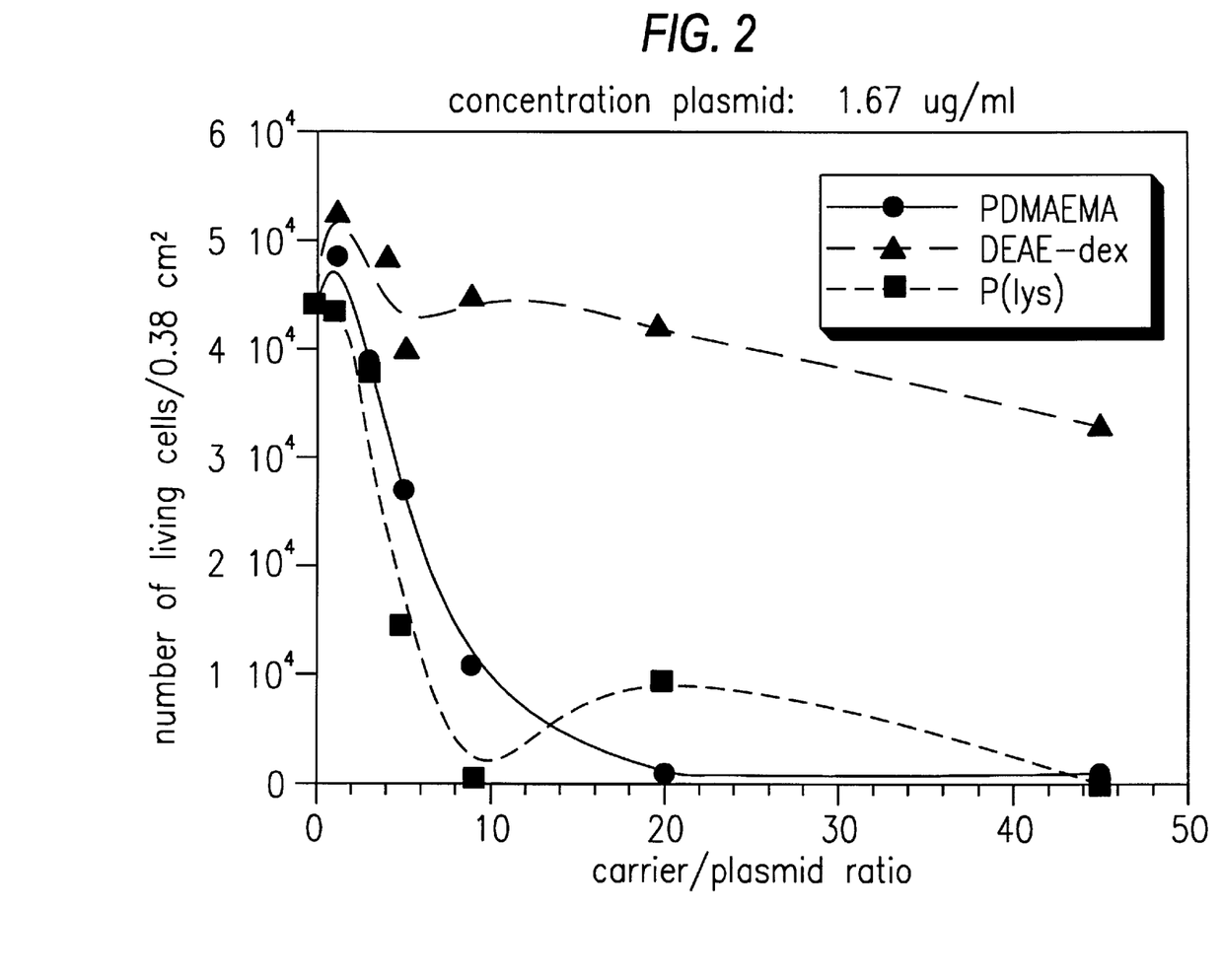
FIG. 2 shows the total number of living cells as a function of carrier/plasmid ratio in the experiment of FIG. 1.

FIG. 2 shows the total number of living cells as a function of the carrier/plasmid ratio. It can be clearly seen that p(lys) is much more cytotoxic than P(DMAEMA). Only marginally cytotoxicity is observed at the concentration of P(DMAEMA) where optimal transfection occurred. DEAE-dextran has a low cytoxicity, however, the transfection efficiency of this polymer is low as compared with P(DMAEMA).

EXAMPLE 2b

Figure 3:
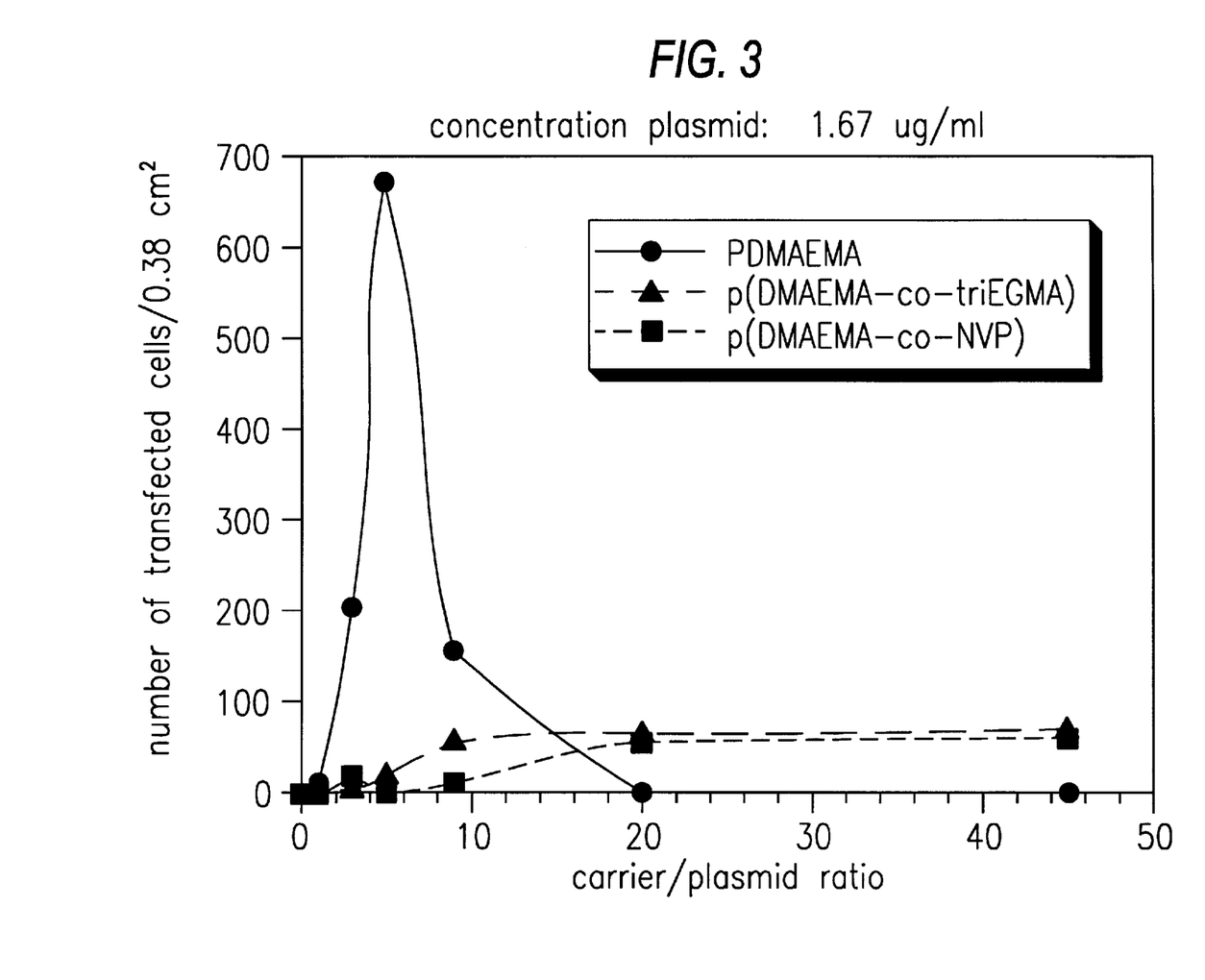
FIG. 3 shows the results of a gene transfer experiment in which the efficiency of two P(DMAEMA) copolymers, P(DMAEMA-co-NVP), copolymer composition DMAEMA/NVP and P(DMAEMA-co-triEGMA) was compared with homo P(DMAEMA).
Figure 4:
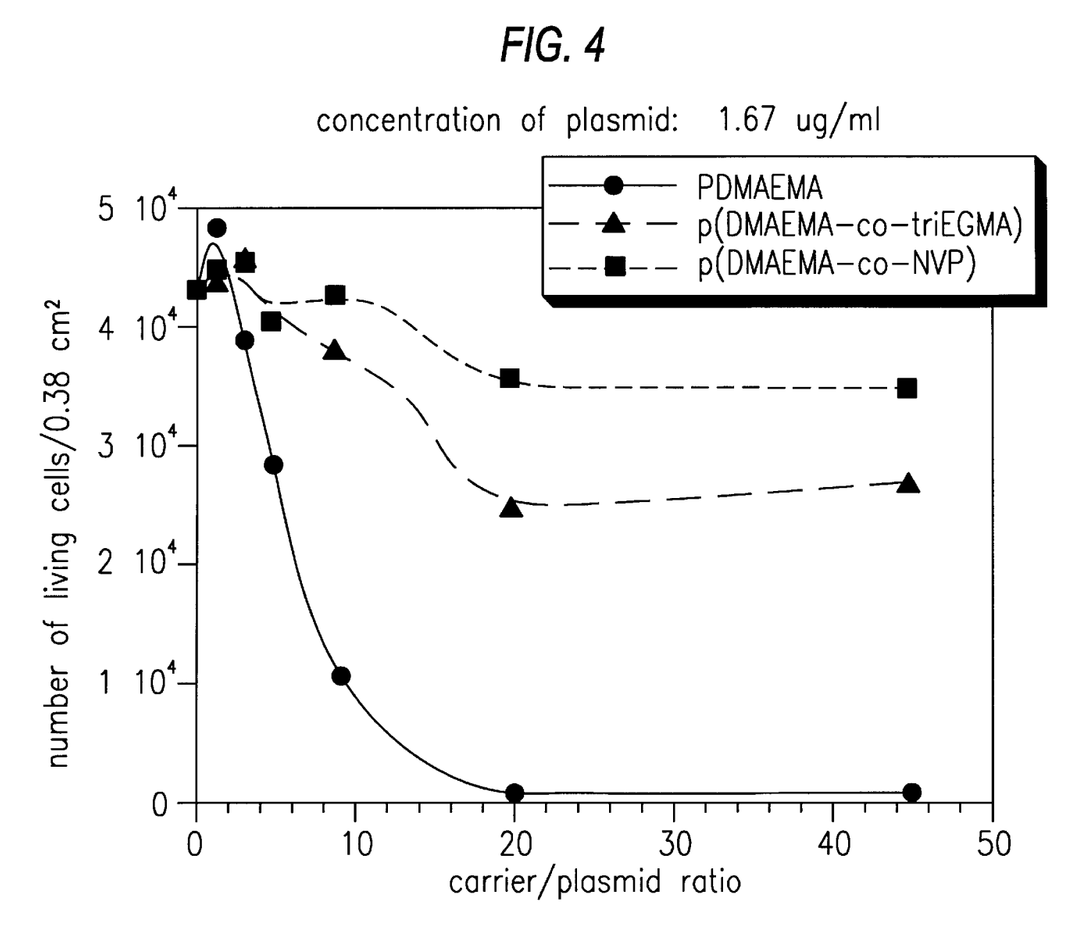
FIG. 4 shows the total number of living cells as a function of the carrier/plasmid ratio in the experiment of FIG. 3.

FIG. 3 shows the results of gene transfer experiment in which the efficiency of 2 P(DMAEMA)copolymers, P(DMAEMA-co-NVP), copolymer composition DMAEMA/NVP 0.3 mole/mole and P(DMAEMA-co-triEGMA), mole ratio 0.8 mole/mole) was compared with homo P(DMAEMA). FIG. 4 shows the total number of living cells as a function of the carrier/plasmid ratio. From these figures it appears that the transfection efficiency of the copolymers is reduced as compared with P(DMAEMA). However, these polymers also exhibit a substantial reduced cytotoxicity.

EXAMPLE 2c

Figure 5:
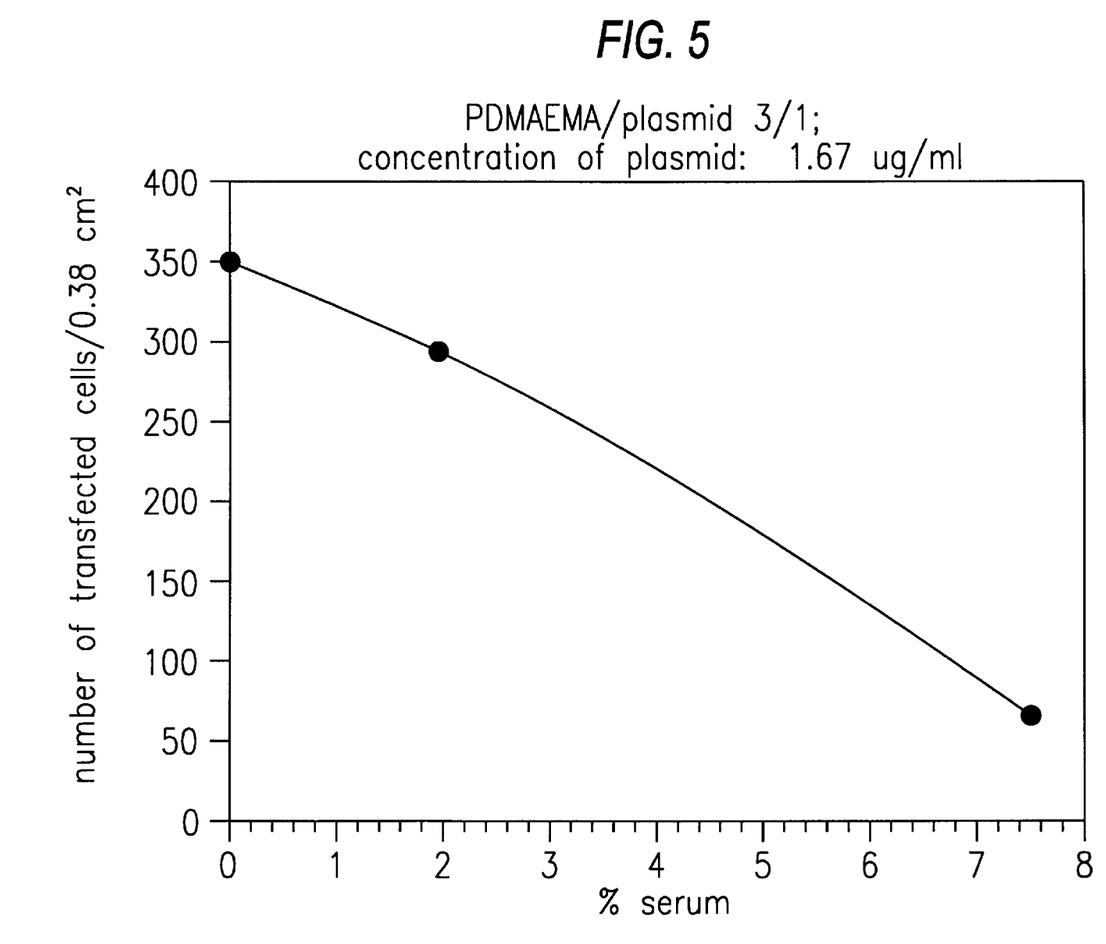
FIG. 5 shows the effect of serum on the transfection efficiency of a PDMAEMA plasmid complex.

FIG. 5 shows the effect of serum on the transfection efficiency of a PDMAEMA/plasmid complex. As a reference, Lipofectin® was used. It is clearly shown that the presence of serum during transfection reduces the number of transfected cells. However, LIPOFECTIN is much more sensitive towards serum than P(DMAEMA): at 2% serum only 10–30 transfected cells/0.38 $cm^2$ were found (LIPOFECTIN/plasmid ratio 3/1; plasmid concentration: 1.6 and 5.0 µg/ml).

EXAMPLE 3

Figure 6:
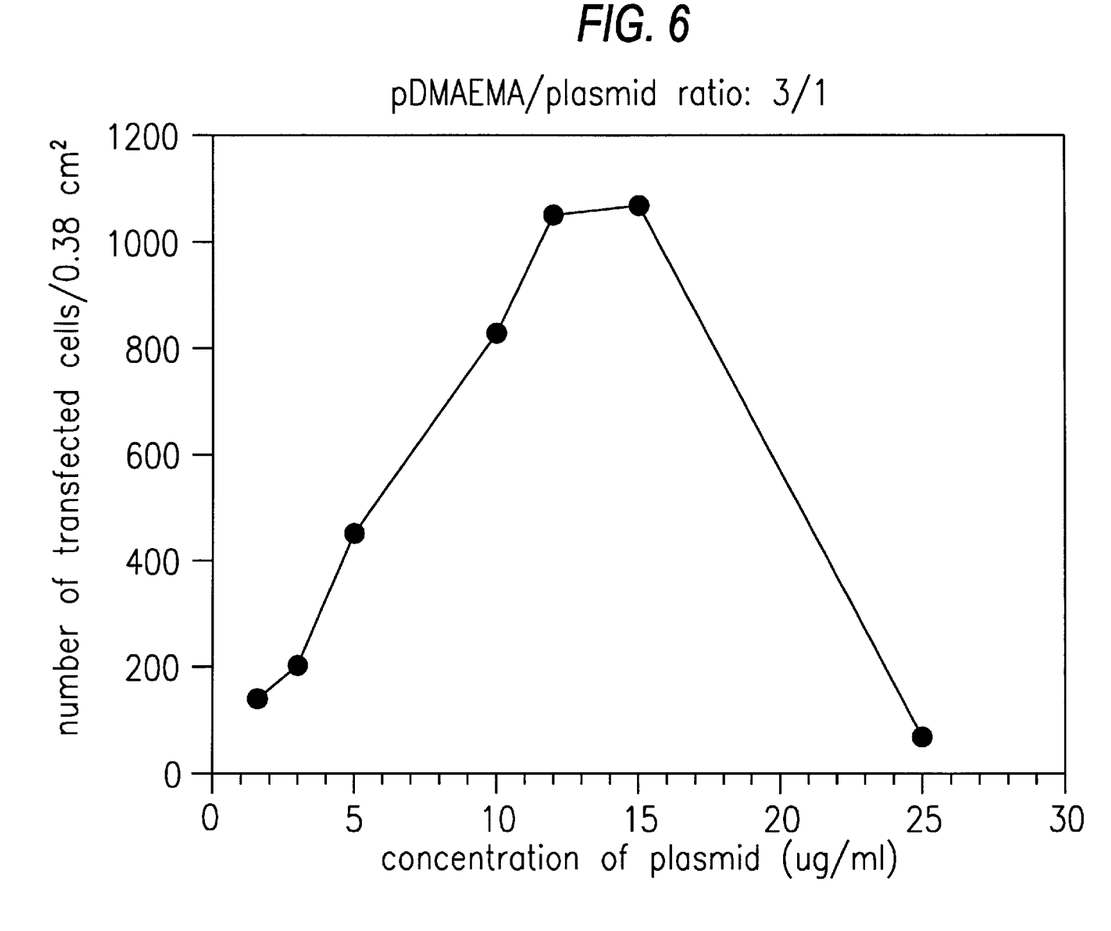
FIG. 6 shows the effect of the number of transfected cells as a function of plasmid concentration.

FIG. 6 shows the effect of the number transfected cells as a function of the plasmid concentration. The plasmid was complexed with P(DMAEMA) at a fixed weight ratio of plasmid and polymer. It can be shown that upto a plasmid concentration of 15 µg/ml, a higher concentration of plasmid/polymer complex concentration resulted in a higher number of transfected cells. At concentrations higher than the 15 µg/ml, the number of transfected cells is decreasing, which is associated with a reduced number of vital cells (about 20% of the cells are vital). The observed cytotoxicity is probably caused by free polymer (=polymer not complexed with the plasmid).

EXAMPLE 4

Figure 7:
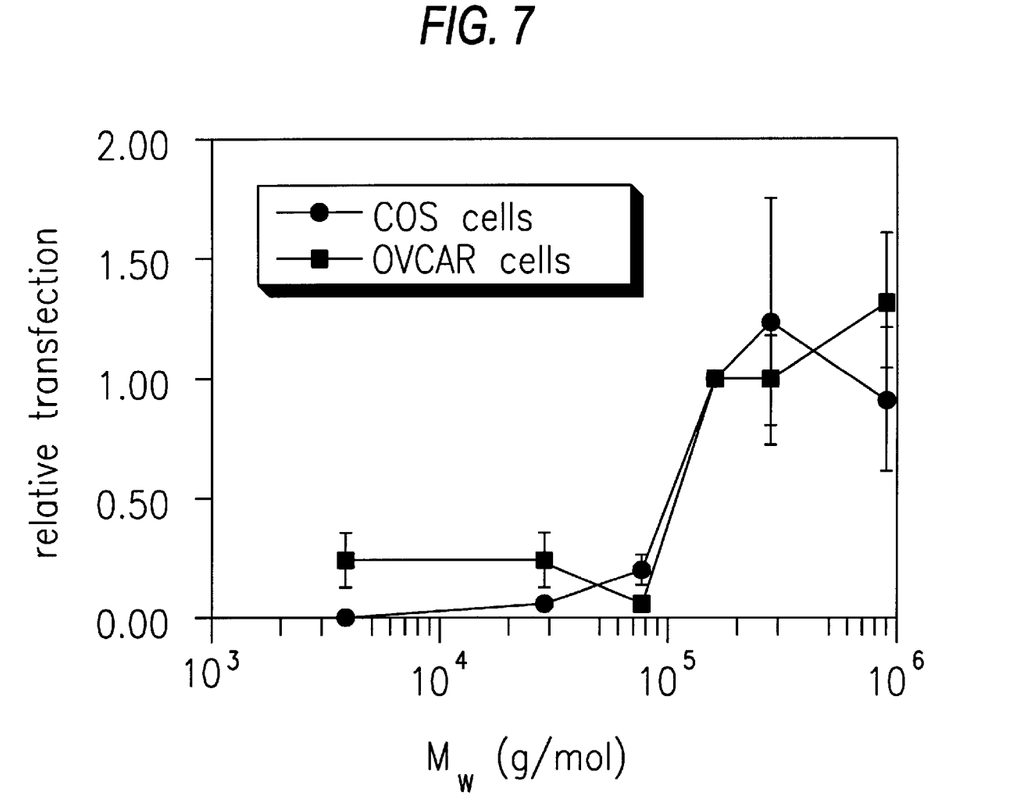
FIG. 7 shows the effect of molecular weight of P(DMAEMA) on transfection efficiency.
Figure 8:
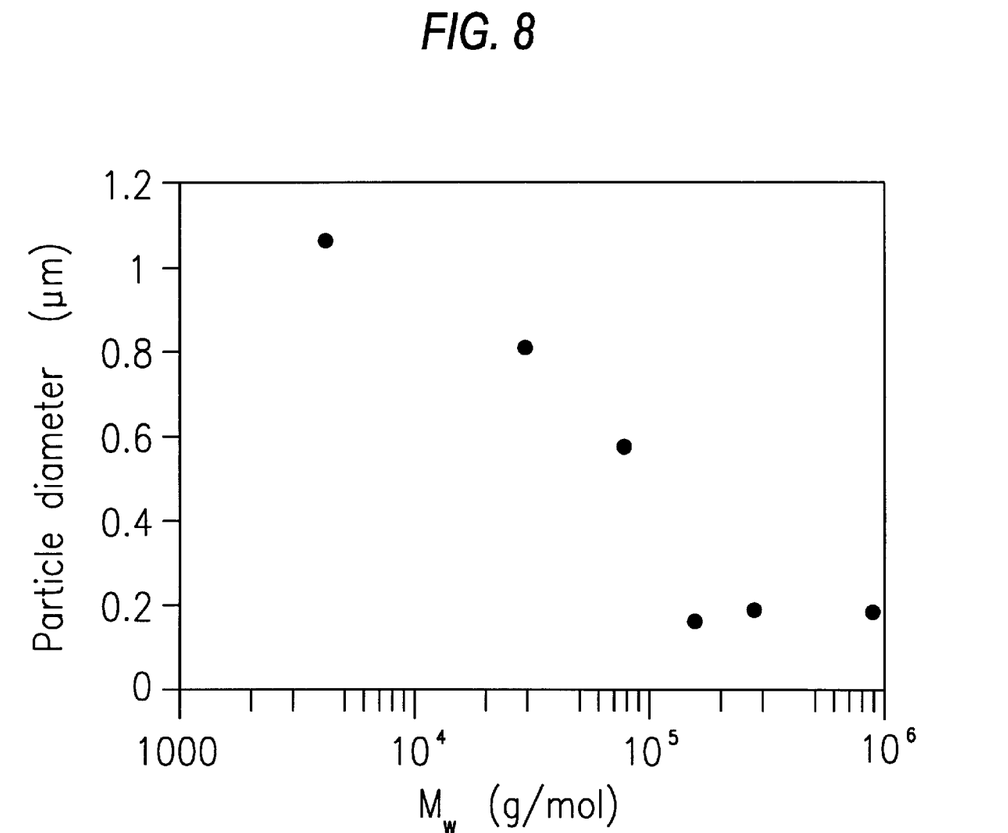
FIG. 8 shows the effect as measured by light scattering measurements of molecular weight on transfection.
Figure 9:
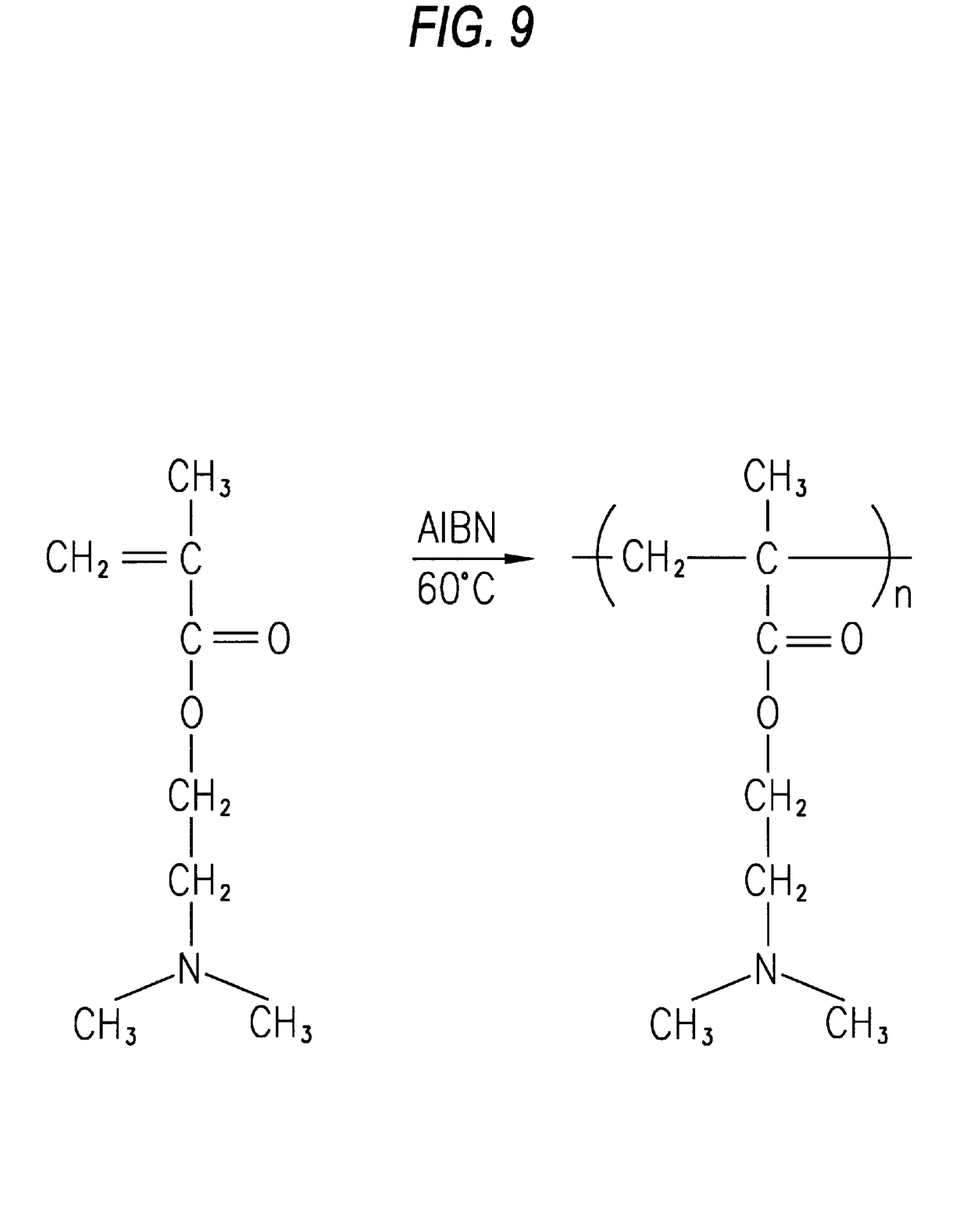
FIG. 9 shows schematically the reaction Used to polymerize DMAEMA.
Figure 10:
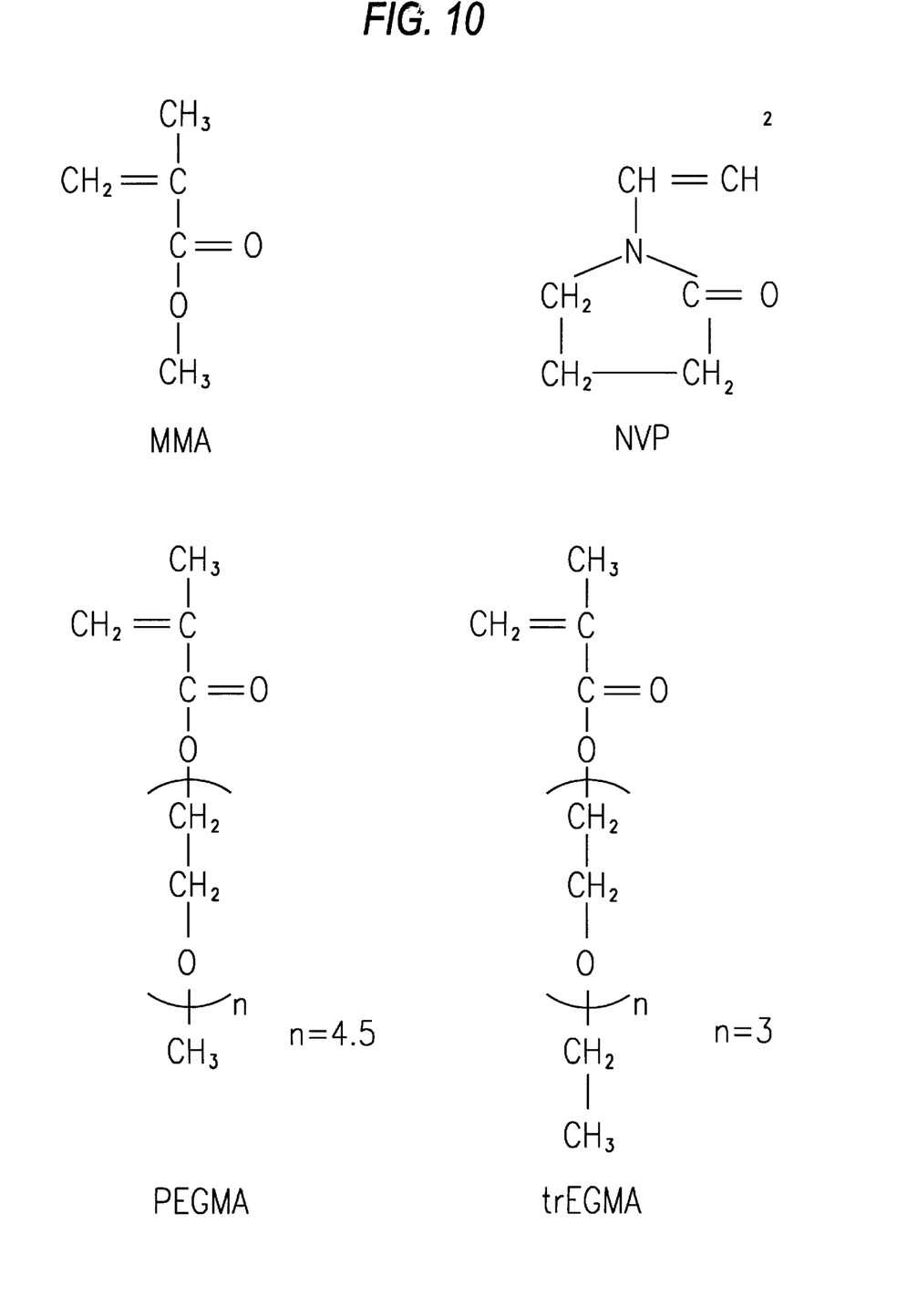
FIG. 10 shows structures of various monomers and polymers useful in the invention.

The transfection efficiency of P(DMAEMA) with varying molecular weights (relative to dextran) was established in COS cells (see example 1) and OVCAR-3 cells (Dr. Hamilton, National Cancer Institute, Bethseda, Md., U.S.A., R. C. Hamiliton et al., Cancer Res. 43, 5379–5389, 1983). Both cell types were cultured as described in example. The transfection efficiency was normalized to the number of transfected cell after incubation with plasmid (1.7 µg/ml in RPMI) complexed to P(DMAEMA) with weight average molecular weight of 156 kDa. The results are shown in FIG. 7. As can be seen, polymers with a molecular weight above 100 kDa are better transfectants than the low molecular weight polymers. Dynamic light scattering measurements showed that these high molecular weight polymers are better condensing agents than the low molecular weight polymers (Polymer/plasmid ratio 5/1 w/w); see FIG. 8).

EXAMPLE 5

The effect of an endosome disruptive peptide on P(DMAEMA)/plasmid complexes was established in COS-7 cells using the protocol given in example 1. The peptide used was the INF4-di (sec C. Plank et al., J. Biol. Chem. 12918–12924, 1994). The $M_W$ of P(DMAEMA) was 360 kDa. The following table 2 gives the results.

TABLE 2

| P(DMAEMA) (µg/ml) | plasmid (µg/ml) | peptide (µg/ml) | number of transfected cells (per 0.38 $cm^2$) |
|---|---|---|---|
| 15 | 0 | 0 | 0 |
| 15 | 5 | 0 | 616 |
| 15 | 5 | 15 | 3668; 3876 (duplicate) |
| 15 | 5 | 45 | 3380 |
| 0 | 5 | 15 | 0 |
| 25 | 5 | 0 | 624 |
| 25 | 5 | 15 | 2860; 3280 (duplicate) |
| 25 | 5 | 45 | 3860 |
| 25 | 5 | 5 | 2082 |

EXAMPLE 6

The following table 3 gives the particular size of polymer/plasmid complexes prepared under different conditions. Polymer Mw=360 Da; incubation time 30 minutes at room temperature, particle size determined by dynamic light scattering; the plasmid and polymer were dissolved in RPMI or 20 mM HEPES, pH 7.4

TABLE 3

| plasmid (µg/ml) | polymer (µg/ml) | buffer | additive | particle size (nm) | poly-dispersity |
|---|---|---|---|---|---|
| 5 | 15 | RPMI | no | 233 ± 1 | 0.20 |
| 10 | 30 | RPMI | no | 230 ± 2 | 0.15 |
| 10 | 30 | RPMI | no | 220 ± 2## | 0.22 |
| 20 | 60 | RPMI | no | 220 ± 5 | 0.26 |
| 30 | 90 | RPMI | no | 260 ± | 0.19 |
| 40 | 120 | RPMI | no | 325# | |
| 50 | 150 | RPMI | no | 300# | |
| 10 | 30 | Hepes | no | 163 ± 4 | 0.17 |
| 30 | 90 | HEPES | no | 200 ± 4 | 0.25 |
| 40 | 120 | HEPES | no | 260 ± 5 | 0.28 |
| 80 | 240 | HEPES | no | 294# | |
| 5 | 15 | RPMI | sucrose* (10%) | 225 ± 4 | 0.20 |
| 5 | 15 | RPMI | sucrose** (10%) | 148 ± 4 | 0.40 |
| 5 | 15 | RPMI | threhalose* (10%) | 247 ± 6 | 0.17 |
| 5 | 15 | RPMI | maltose* (10%) | 227 ± 1 | 0.20 |
| 5 | 15 | HEPES | sucrose* (10%) | 117 ± 3 | 0.33 |
| 5 | 15 | HEPES | sucrose** (10%) | 106 ± 2 | 0.37 |
| 15 | 45 | HEPES | sucrose* (10%) | 149 ± 1 | 0.24 |
| 15 | 45 | HEPES | sucrose** (10%) | 101 ± 1 | 0.33 |
| 40 | 120 | HEPES | sucrose** (10%) | 174 ± 1 | 0.26 |

*added after the formation of the complex
**present during particle formation
aggregation
after freezing (−20° C.) and thawing (room temperature)

It appears that small particles can be prepared when the polymer and plasmid are complexed in the presence of sucrose.

We claim:

1. A synthetic transfection system comprising
   a carrier which is a cationic, water soluble or water dispersible polyacrylate or poly($C_{1-6}$ alkyl)acrylate or the corresponding acrylamides, and
   a nucleic acid fragment.

2. The system according to claim 1, wherein said nucleic acid fragment is a plasmid, a gene construct, or an oligonucleotide.

3. The system of claim 1, wherein said carrier is a homo or copolymer of dimethyl amino ethyl methacrylate.

4. The system of claim 1 wherein the carrier is coupled to a fusogenic structure.

5. A method to introduce DNA fragments into target cells which comprises contacting said cells with the transfection system of claim 1.

6. The system of claim 1, wherein condensed particles comprising said synthetic transfection system is enclosed in a drug delivery system.

7. The system of claim 6 wherein said drug delivery system comprises liposomes or a hydrogel.

8. The system of claim 1, wherein the carrier is coupled to an agent which targets the surface of a cell population.

9. The system of claim 8, wherein the agent which targets the surface of a cell population is a monoclonal antibody which recognizes a protein present in the cellular membrane of a target cell.

10. A method for the preparation of a synthetic transfection system comprising contacting nucleic acid fragments with a cationic water soluble or water dispersible polyacrylate or poly($C_{1-6}$ alkyl)acrylate, or the corresponding acrylamides under conditions wherein the polymer is positively charged.

11. The method of claim 10, wherein the contacting is carried out in the presence of a viscosity increasing substance.

12. The method of claim 11, wherein said viscosity increasing substance is sucrose.

* * * * *